(12) United States Patent
Wilsak et al.

(10) Patent No.: US 8,211,319 B2
(45) Date of Patent: Jul. 3, 2012

(54) SOLID-LIQUID SEPARATION PROCESS

(75) Inventors: Richard A. Wilsak, Naperville, IL (US);
Scott A. Roberts, Naperville, IL (US);
Dean B. Comstock, Batavia, IL (US);
Ronald Stefanski, Aurora, IL (US);
George A. Huff, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 659 days.

(21) Appl. No.: 10/663,918

(22) Filed: Sep. 16, 2003

(65) Prior Publication Data

US 2005/0056599 A1  Mar. 17, 2005

(51) Int. Cl.
*B01D 37/00* (2006.01)
*C07C 7/14* (2006.01)

(52) U.S. Cl. ......... 210/767; 210/808; 585/812; 585/814

(58) Field of Classification Search ................... 210/767, 210/770, 771, 772, 248
See application file for complete search history.

(56) References Cited

U.S. PATENT DOCUMENTS

| | | | |
|---|---|---|---|
| 1,612,773 A | | 6/1931 | Cannon |
| 2,377,935 A | * | 6/1945 | Gunness ................. 208/160 |
| 2,394,814 A | * | 2/1946 | Snuggs ................. 208/150 |
| 2,428,691 A | * | 10/1947 | Tyson ................. 208/150 |
| 2,472,377 A | * | 6/1949 | Keith ................. 518/712 |
| 2,488,031 A | * | 11/1949 | Gunness ................. 208/152 |
| 2,663,676 A | * | 12/1953 | Cardwell et. al. ............. 208/157 |
| 2,718,308 A | * | 9/1955 | Le Bus ................. 210/532.1 |
| 2,780,663 A | | 2/1957 | Guinness |
| 2,813,781 A | | 11/1957 | Mertes ................. 23/310 |
| 2,851,161 A | | 9/1958 | Dahlstrom et al. |
| 2,854,494 A | | 9/1958 | Thomas |
| 2,885,431 A | | 5/1959 | Tarr |
| 2,886,603 A | * | 5/1959 | Shelton ................. 568/940 |
| 2,903,343 A | * | 9/1959 | Weedman ................. 422/251 |
| 3,177,265 A | * | 4/1965 | Lammers ................. 585/815 |
| 3,217,942 A | * | 11/1965 | Humbert, Jr. et al. ... 222/189.06 |
| 3,319,437 A | | 5/1967 | Goins ................. 62/123 |
| 3,469,369 A | | 9/1969 | Helmke |
| 3,524,548 A | * | 8/1970 | McDonald et al. ........... 210/153 |
| 3,696,930 A | * | 10/1972 | Tokura ................. 210/225 |
| 3,772,998 A | * | 11/1973 | Menigat ................. 110/222 |
| 3,804,915 A | * | 4/1974 | Schmid et al. ............... 585/801 |
| 3,992,298 A | * | 11/1976 | Davis ................. 210/141 |
| 4,008,158 A | * | 2/1977 | Davis ................. 210/386 |

(Continued)

FOREIGN PATENT DOCUMENTS

CH  0497910  12/1970

(Continued)

OTHER PUBLICATIONS

Search #98-0447 Subject: Apparatus for the Separation of Solids Particles from a Liquid Suspension—Dec. 16, 1998—Disclosure No. 38,060.

(Continued)

*Primary Examiner* — Robert James Popovics

(57) ABSTRACT

A process for separating solids from liquids in a filtration zone defined by a higher concentration zone and a lower concentration zone separated by a filter. The process includes the steps of directing a slurry feed comprising a liquid and solids into the higher concentration zone, directing a displacement fluid to the higher concentration zone and passing at least a portion of the liquid through a filter to the filtrate zone, producing a filtrate.

20 Claims, 2 Drawing Sheets

U.S. PATENT DOCUMENTS

| | | | | |
|---|---|---|---|---|
| 4,018,579 A | * | 4/1977 | Hofmann | 96/111 |
| 4,053,268 A | * | 10/1977 | Kishino | 425/84 |
| 4,093,672 A | * | 6/1978 | Sun | 585/801 |
| 4,247,310 A | * | 1/1981 | Borst | 95/26 |
| 4,270,937 A | | 6/1981 | Adler et al. | 62/17 |
| 4,341,085 A | * | 7/1982 | Nail | 62/124 |
| 4,344,781 A | * | 8/1982 | Higgins et al. | 55/379 |
| 4,453,959 A | | 6/1984 | Bishkin | 62/542 |
| 4,517,806 A | * | 5/1985 | Korzonas | 62/123 |
| 4,623,372 A | | 11/1986 | Adler et al. | 62/532 |
| 4,687,497 A | * | 8/1987 | Owen et al. | 55/349 |
| 4,734,102 A | | 3/1988 | Thijssen et al. | 23/296 |
| 4,735,781 A | * | 4/1988 | Thijssen et al. | 422/251 |
| 4,769,219 A | * | 9/1988 | Tasker et al. | 422/144 |
| 4,792,391 A | * | 12/1988 | Cox | 208/108 |
| 4,902,407 A | * | 2/1990 | Chan et al. | 208/152 |
| 4,933,150 A | * | 6/1990 | Haddad et al. | 422/147 |
| 5,004,860 A | * | 4/1991 | Hansen et al. | 585/812 |
| 5,051,194 A | * | 9/1991 | Bahr | 210/770 |
| 5,104,519 A | * | 4/1992 | Haddad et al. | 208/152 |
| 5,145,497 A | * | 9/1992 | Maeda | 96/409 |
| 5,292,434 A | | 3/1994 | Benesi | 210/770 |
| 5,387,406 A | | 2/1995 | Ruoff | 423/210 |
| 5,565,090 A | * | 10/1996 | Gosling et al. | 208/134 |
| 5,589,079 A | * | 12/1996 | Park et al. | 210/784 |
| 5,643,468 A | | 7/1997 | Ure | 210/771 |
| 5,707,512 A | | 1/1998 | Koch et al. | |
| 5,770,045 A | * | 6/1998 | Gosling et al. | 208/137 |
| 6,068,760 A | | 5/2000 | Benham et al. | 518/700 |
| 6,341,567 B1 | * | 1/2002 | Robertson et al. | 110/203 |
| 6,491,817 B1 | * | 12/2002 | Benesi | 210/227 |
| 6,521,135 B1 | * | 2/2003 | Benesi | 210/771 |
| 6,620,243 B1 | * | 9/2003 | Bertellotti et al. | 118/621 |
| 6,652,760 B2 | * | 11/2003 | Anderson | 210/767 |
| 6,712,982 B2 | * | 3/2004 | Bohn et al. | 210/802 |
| 6,730,221 B2 | * | 5/2004 | Bohn et al. | 210/251 |
| 7,078,439 B2 | * | 7/2006 | Odueyungbo et al. | 518/700 |
| 2003/0127401 A1 | | 7/2003 | Benesi | |
| 2005/0056599 A1 | * | 3/2005 | Wilsak et al. | 210/767 |
| 2006/0013748 A1 | * | 1/2006 | Nordhoff et al. | 422/188 |
| 2007/0225539 A1 | * | 9/2007 | Wilsak et al. | 585/812 |

FOREIGN PATENT DOCUMENTS

| | | |
|---|---|---|
| DE | 2921871 | 12/1960 |
| DE | 1197421 | 7/1965 |
| DE | 1619940 | 6/1970 |
| DE | 1937286 | 2/1972 |
| DE | 1643724 | 4/1972 |
| DE | 3211865 | 10/1983 |
| EP | 0175401 | 8/1985 |
| EP | 1080768 | 3/2001 |
| FR | 1352915 | 1/1964 |
| GB | 1308054 | 2/1973 |
| NL | 0398437 | 11/1990 |

OTHER PUBLICATIONS

Invention Disclosure Questionnaire—Apparatus for the Separation of Solids Particles from a Liquid Suspension. Amoco Chemical Company—Chemical Feedstock Business Group, Project No. 6042102.
Paraxylene Wash Column Technology Ucense Agreement between TNO and Amoco effective Mar. 7, 1994.

* cited by examiner

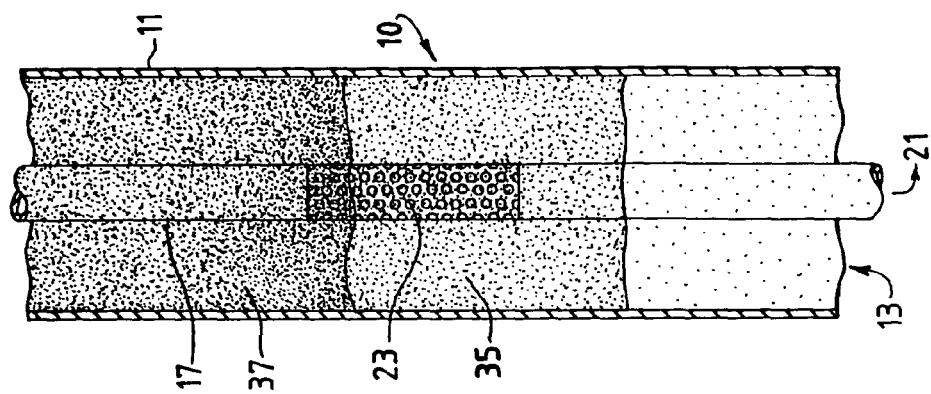
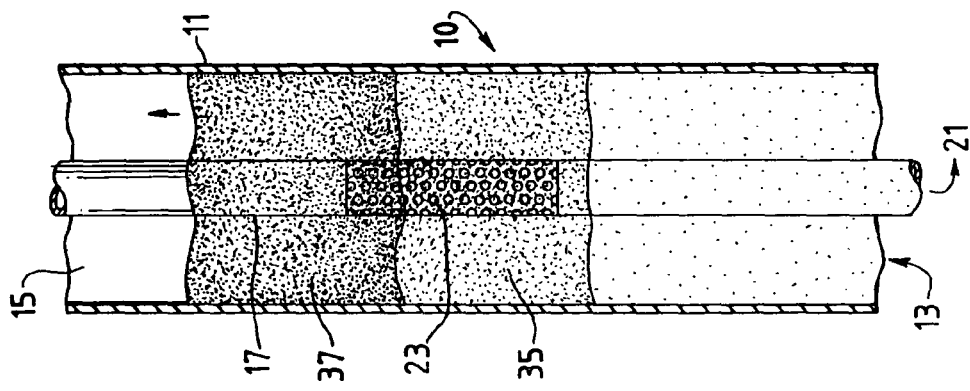
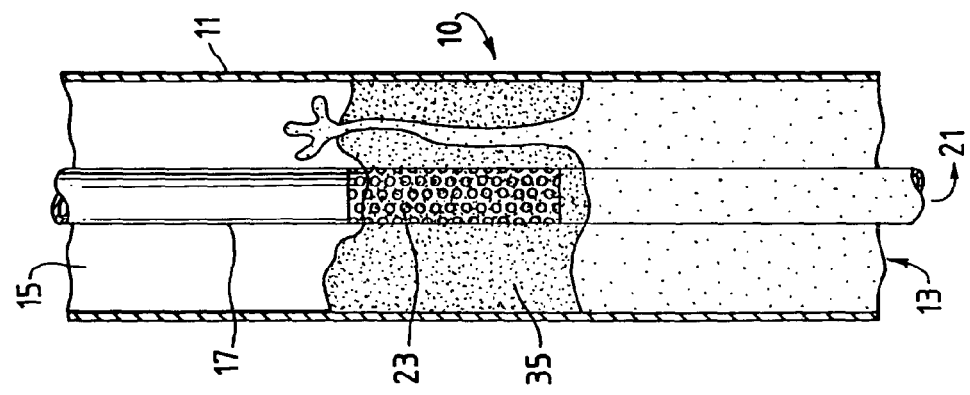
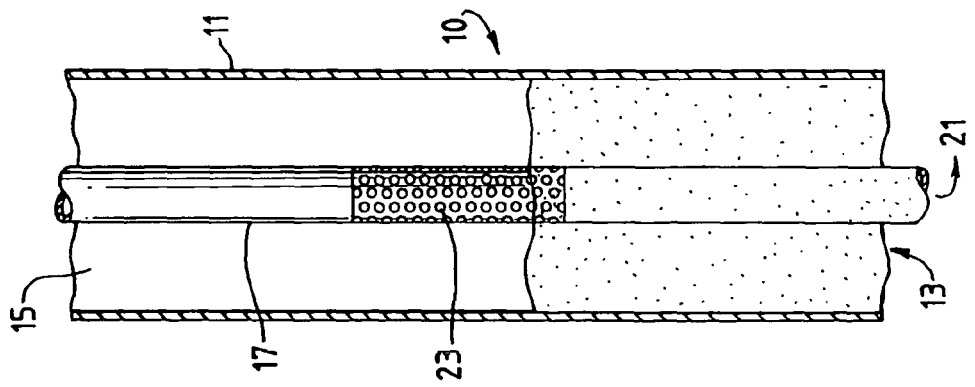

SOLID-LIQUID SEPARATION PROCESS

FIELD OF INVENTION

The present invention relates to a process for separating liquid(s) from solids in a slurry feed.

BACKGROUND OF THE INVENTION

Solid-liquid separation methods are important in a variety of industries, including, but not limited to, the chemical industry, the pharmaceutical industry, and the water and waste treatment industry. Such solid-liquid separation methods vary, and may include, but are not limited to, vacuum or pressure filtration, centrifugation, sedimentation and clarification. In many chemical processes, these solid-liquid separation methods often play a critical role in the manufacture of particular chemical intermediates. For instance, the purification of para-xylene for the manufacture of terephthalic acid has historically required centrifugation to achieve para-xylene purity levels of about 99.7%.

The purification of para-xylene typically begins with a $C_8$ aromatic hydrocarbon feed that typically comprises ethylbenzene and mixture of xylene isomers, such as ortho-xylene, meta-xylene and para-xylene. Processes to separate these xylene isomers include low temperature crystallization, fractional distillation and adsorption.

Crystallization is often preferred for separating para-xylene from the $C_8$ aromatic feedstream because while xylene isomers have undesirably similar boiling points, they have dramatically different melting points. Pure para-xylene freezes at 56° F., pure meta-xylene freezes at −54° F., pure ortho-xylene freezes at −13° F., and pure ethylbenzene freezes at −139° F.

The recovery and purification of para-xylene from a mixture of xylene isomers by crystallization are typically limited by the formation of one or the other of two binary eutectics, the para-xylene/meta-xylene binary eutectic or the para-xylene/ortho-xylene binary eutectic. Depending on the starting composition of the mixture, para-xylene will crystallize from the mixture as the temperature of the mixture is lowered, and the mother liquor composition will approach one of the binary eutectic compositions. If the temperature falls below either of the binary eutectic temperatures, then a second solid phase which is lean in para-xylene will crystallize from the mixture. The formation of a second solid phase is generally viewed as undesirable so crystallization processes are typically operated at a temperature warmer than the warmest binary eutectic temperature. While this limits the recovery of the process, conventional para-xylene separation processes that use crystallization produce a substantially pure para-xylene product.

For example, U.S. Pat. No. 3,177,265, which is incorporated herein by reference, illustrates a conventional indirect-cooled crystallization process for purifying para-xylene. In this process, a $C_8$ aromatic feedstream comprising about 20 percent para-xylene with the remaining components ortho-xylene, meta-xylene, and ethylbenzene is crystallized in a series of crystallization stages to form a mixed xylene slurry while utilizing costly centrifugation steps to separate the slurry into a crystal cake and a liquid filtrate. This para-xylene purification process produces a para-xylene product with a purity in excess of 98 percent.

Although such processes produce a para-xylene product with a purity level in excess of 98 percent, the use of centrifuges add significant costs to the purification process due to their high capital costs and the high maintenance costs inherent in high speed rotating parts. As a result, prior efforts have focused on developing alternatives to centrifugation to improve the economics of producing substantially pure para-xylene.

Two such efforts are U.S. Pat. Nos. 4,734,102 and 4,735,781, to Thijssen which disclose an apparatus and process for concentrating a suspension. The Thijssen apparatus, called a hydraulic wash column, is directed to a hollow cylinder in which one or more tubes of a constant outer diameter extend in an axial direction within the wall of each tube comprising at least one filter being mounted forming the only direct connection between the interior of the tube and the interior of the hollow cylinder.

The Thijssen process separates solids from liquids by directing a suspension into a first end of the hydraulic wash column and a wash liquid into a second end of the hydraulic wash column in countercurrent flow to the suspension, forming a bed in the hollow cylinder. A filtrate (mother liquor) from the suspension escapes through the filters of the filter tubes into the interior of the tubes, and a concentrated suspension is withdrawn from the second end of the hydraulic wash column. A liquid is introduced at the second end to reslurry the concentrated suspension. This liquid also acts as the wash liquid. When the process is used to separate a suspension derived from a melt crystallization process, the wash liquid comprises molten crystal product from the suspension.

Although the Thijssen patents teach an alternative method and apparatus for solid-liquid separation, the Thijssen process cannot effectively separate liquids from solids at temperatures far below the melting point of crystals in slurries derived from a melt crystallization process because the wash liquid utilized during the process freezes within the Thijssen hydraulic wash column during the washing part of the operation. At lower and lower temperatures, the freezing wash liquid fills a larger portion of the void fraction between the solids thereby requiring higher and higher pressures to drive the wash liquid into the column. Eventually, a low enough temperature will be reached wherein the freezing wash liquid essentially plugs the device causing failure and imminent shutdown of the Thijssen apparatus and process.

Additionally, the use of a molten solids wash liquid in the Thijssen process can contaminate the filtrate with a liquid that cannot easily be separated from the filtrate and result in a substantial loss of solid product to the filtrate.

Consequently, there is still a need for alternative methods and apparatuses for solid-liquid separation that: (1) separate liquids from solids in slurries derived, for example, from a crystallization process without the unnecessary loss of solids to the filtrate during the separation process; (2) direct separated filtrates and/or product cakes for further processing without significant energy and/or cost penalties; and (3) operate cooperatively and in conjunction with conventional unit operations.

It has now been found that feeding a displacement fluid, such as a gas, in lieu of a wash liquid produces a relatively dry and pure product with sufficient solids content that can be further processed with little or no additional refrigeration costs.

It has also been found that separating liquids from solids in a filter column, as described herein, at temperatures far below the melting point of crystals in slurries derived from a crystallization process can be operated in a continuous manner without high loss of the crystals to the liquid filtrate through one or more filters during the separation process.

It has also been found that passing a substantial portion of a displacement fluid through a solid packed bed of crystals to one or more filters can result in an acceptably pure solid product.

SUMMARY OF THE INVENTION

Therefore, the present invention is directed to a process for separating solids from liquids in a filtration zone defining a higher concentration zone and a lower concentration zone separated by a filter, the process comprising the steps of directing a slurry feed comprising a liquid and a solid into the higher concentration zone, directing a displacement fluid to the higher concentration zone, and passing at least a portion of the liquid through a filter to the lower concentration zone, producing a filtrate.

In another embodiment, the invention is directed to a process for maintaining a solid phase throughout the separation of liquids from solids in a filtration zone defined by a higher pressure zone and a lower pressure zone separated by a filter, the process comprising the steps of imparting a pressure on a slurry feed comprising a liquid and a solid in the higher pressure zone, imparting an opposing pressure on the slurry feed in the higher pressure zone, depositing at least a portion of the solids at the filter, forming a solid packed bed in the higher pressure zone, and maintaining the higher pressure zone at a temperature lower than the melting point of at least one solid in the slurry feed.

In still another embodiment, the invention is directed to a process for separating solids from liquids in a filtration zone defined by a higher pressure zone and a lower pressure zone separated by a filter, the process comprising the steps of directing a slurry feed comprising a liquid and a solid into the higher pressure zone, directing a fluid into the higher pressure zone in countercurrent relation to the slurry feed, embedding at least a portion of the solids in proximity to the filter, forming a solid packed bed in the higher pressure zone, and passing at least a portion of the fluid through a filter to the lower pressure zone.

The present invention provides for efficient separation of crystallized products from a slurry feed stream at relatively low temperatures without the risk and attendant penalties associated with the freezing of a wash liquid within the filter column and causing complete failure of the solid-liquid separation process.

The present invention also provides for the possibility of varying the purity of a solid product separated from a slurry feed by simply varying the flow rate of the displacement fluid or the temperature of the displacement fluid that is directed in countercurrent relation to the slurry feed.

The present invention also provides for a substantial reduction in capital expenditure and routine maintenance by reducing the number of moving parts required by solid-liquid separation process units, such as screen bowl and pusher centrifuges.

The present invention also provides for substantial savings in refrigeration costs by allowing for solid-liquid separation of crystallization products under substantially isothermal conditions.

The present invention also provides for a substantial cost savings by reducing the high amount of solids lost in filtrate streams frequently found in conventional solid-liquid separation processes and apparatuses.

BRIEF DESCRIPTION OF THE DRAWING

FIGS. 2a-d depict an embodiment of a start-up procedure for a filter column and filtration process in accordance with the subject invention.

DESCRIPTION OF THE PREFERRED EMBODIMENTS

Figure 1:
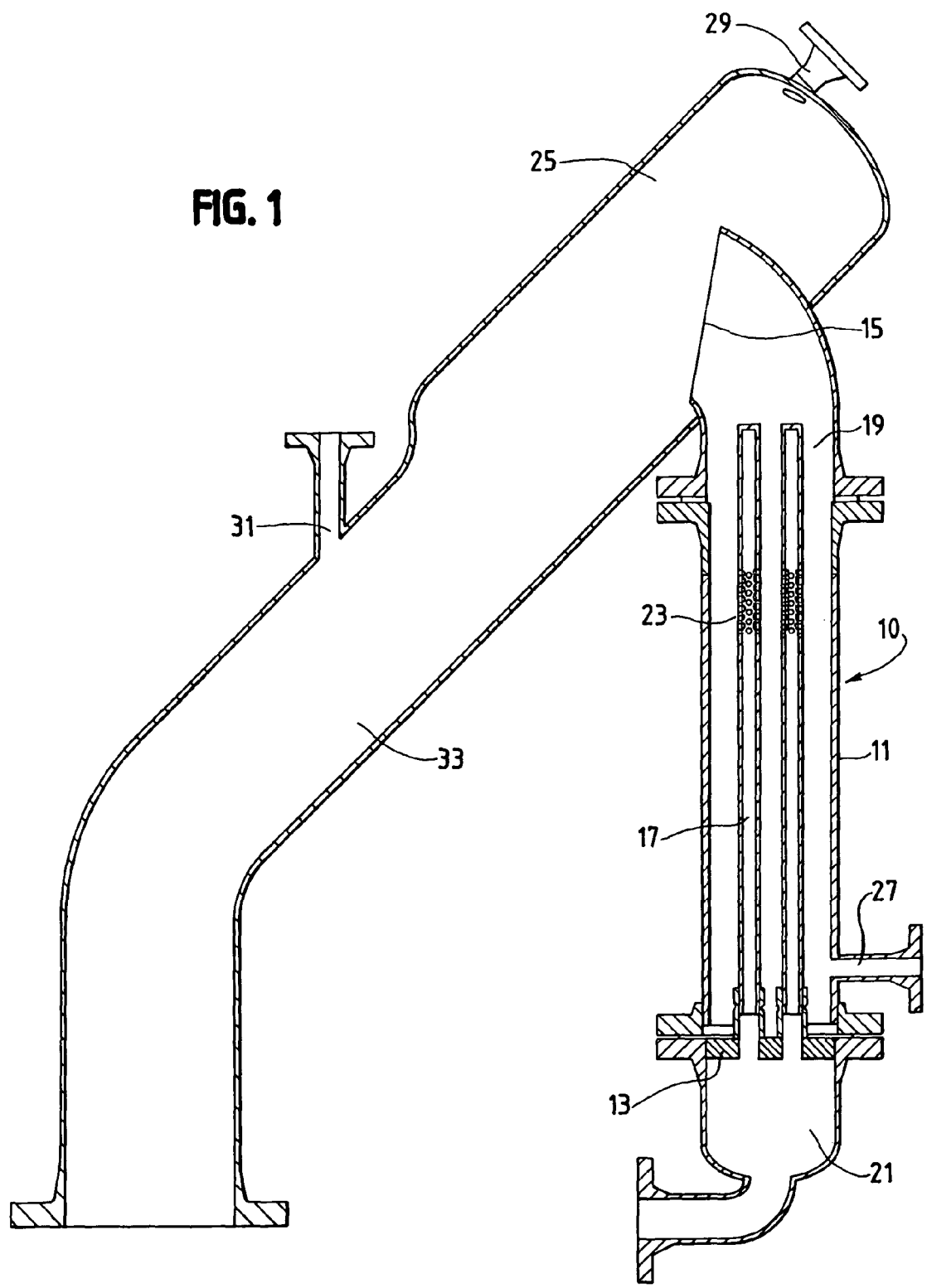
FIG. 1 depicts an embodiment of a filter column and filtration process in accordance with the subject invention.

In greater detail, slurry feeds suitable for the subject invention can be any mixture of suspended solids and liquids. Such slurry feeds may be light slurries, medium slurries and heavy slurries. The light slurries are typically slurries that are not intended to carry solids and are typically non-settling. Light slurries may have a solid size of less than about 200 microns, a specific gravity of less than about 1.05, and comprise less than about 5 weight percent solids. Medium slurries can be settling or non-settling slurries. Medium slurries may have a solid size of from about 200 microns to about 6.4 mm, a specific gravity of from about 1.05 to about 1.15, and comprise from about 5 to about 20 weight percent solids. Heavy slurries are typically slurries that are designed to transport material from one location to another and can be settling or non-settling. Heavy slurries may have a solid size greater than about 6.4 mm, a specific gravity greater than about 1.15, and comprise at least about 20 weight percent solids.

In a preferred embodiment, the slurry feed comprises at least about 0.5 weight percent solids. It is also preferred that the slurry feed comprises at least about 10 weight percent solids, and more preferably at least about 15 weight percent solids. It is also preferred that the slurry feed comprise less than about 65 weight percent solids, more preferably less than about 60 weight percent solids, and even more preferably less than about 55 weight percent solids. It is also preferred that the slurry feed comprises from about 0.5 to about 65 weight percent solids, more preferably from about 10 to about 60 weight percent solids, and more preferably from about 15 to about 55 weight percent solids for best results.

In a preferred embodiment, the slurry feed is a product from a crystallization process. Such products may include, but are not limited to, products from the crystallization of para-xylene, protein, water, acrylic acid, and methacrylic acid.

In a preferred embodiment, the slurry feed comprises at least about 5 weight percent crystallized para-xylene, more preferably at least about 10 weight percent crystallized para-xylene, and more preferably at least about 15 weight percent crystallized para-xylene. It is also preferred that the slurry feed comprise less than about 65 weight percent crystallized para-xylene, more preferably less than about 60 weight percent crystallized para-xylene, and even more preferably less than about 55 weight percent crystallized para-xylene. It is also preferred that the slurry feed comprises from about 5 to about 65 weight percent crystallized para-xylene, more preferably from about 10 to about 60 weight percent crystallized para-xylene, and more preferably from about 15 to about 65 weight percent crystallized para-xylene for best results.

A displacement fluid suitable for the subject invention can be a gas or liquid capable of displacing the liquid from the slurry feed as described herein. In a preferred embodiment, the gas is an inert gas, such as nitrogen or carbon dioxide. In another preferred embodiment, the gas is air. In yet another preferred embodiment, the gas can be hydrogen. A suitable displacement fluid can also be a liquid insoluble in one or more solids of the slurry feed. In a preferred embodiment, the displacement fluid is also insoluble in one or more liquids of the slurry feed, allowing for relatively easy subsequent separation of the displacement fluid from the filtrate.

The displacement fluid can be at any temperature suitable for separating liquid from solids in a particular slurry feed. However, in a preferred embodiment, the displacement fluid is at a temperature lower than the temperature of the slurry feed. The lower temperature of the displacement fluid can be utilized to further crystallize at least a portion of the liquid or maintain crystal form in the slurry feed, providing for higher solids recovery. In another embodiment, the displacement fluid is at a higher temperature than the temperature of the slurry feed. The higher temperature of the displacement fluid can be utilized to facilitate the removal of residual liquid from the solid packed bed, producing a purer concentrated product. In yet another embodiment, the temperature of the displacement fluid is about the same as the temperature of the slurry feed in order to practice the solid-liquid separation process isothermally. In another embodiment, wherein the displacement fluid is a gas and the amount of gas is small compared to the amount of solids in the slurry, the temperature of the displacement fluid is relatively immaterial as the amount of energy introduced to the device by the gas is insignificant and the unit operates at essentially isothermal conditions over a wide range of gas temperatures.

A filter column suitable for the subject invention comprises a filtration zone defined by a higher concentration zone and a lower concentration zone separated by a filter. The higher concentration zone has a greater weight percent of solids than the lower concentration zone. This concentration differential can be measured by any means suitable to demonstrate a concentration gradient across a filter in the filtration zone. For example, the concentration of solids in the higher concentration zone can be determined by measuring the weight percent of solids in the slurry feed directed into the higher concentration zone, and the concentration of solids in the lower concentration zone can be determined by measuring the weight percent of solids in a filtrate withdrawn from the filter column.

Alternatively, the filtration zone can be defined by a higher pressure zone and a lower pressure zone separated by a filter. The higher pressure zone is at a higher pressure than the lower pressure zone. This pressure differential can be measured by any means suitable to demonstrate a pressure gradient across a filter in the filtration zone. For example, the pressure of the higher-pressure zone can be determined by measuring the pressure of the slurry feed directed into the higher pressure zone, and the pressure of the lower pressure zone can be determined by measuring the pressure of a filtrate withdrawn from the filter column. Additionally, fluids flow from areas of high pressure to areas of low pressure. Consequently, the flow of fluid through the filter indicates a pressure differential between the higher pressure zone and the lower pressure zone across the filter.

Referring to FIG. 1, a preferred filter column 10 comprises a hollow cylinder 11 having a closed end 13 and an open end 15, and at least one filter tube 17 extending in an axial direction within the cylinder 11, at least one filter tube 17 having a top portion 19 and a bottom portion 21 wherein the bottom portion 21 of at least one filter tube 17 extends through the closed end 13 of the hollow cylinder 11, the bottom portion 21 having an opening at a terminal end. At least one filter tube 17 comprises at least one filter 23 integrally attached to at least one filter tube 17 forming a direct connection for fluid flow between the interior of the filter tube 17 and the interior of the hollow cylinder 11. In this preferred embodiment, the interior of the hollow cylinder surrounding the filter tubes 17 defines the higher concentration zone or higher pressure zone and the interior of the filter tubes 17 defines the lower concentration zone or lower pressure zone.

Filter column 10 further comprises at least one chamber 25 through which the open end 15 of the hollow cylinder 11 is exposed. At the closed end 13 of the cylinder 10, it is preferred that there is at least one slurry feed inlet 27 to direct a slurry feed into the hollow cylinder 11. Filter column 10 further may comprise at least one displacement fluid inlet line 29 to direct a displacement fluid preferably into the chamber 25 and/or the hollow cylinder 11. Filter column 10 may also comprise at least one product chute 33 having an opening to the chamber 25 to withdraw concentrated solids from the chamber 25. Filter column 10 may further comprise at least one flush line 31 to direct a flush feed into the product chute 33 to clear the product chute 33 of obstructions, such as packed concentrated solids lodged in the product chute 33. Filter column 10 may further comprise a set of rotatable blades (not shown) to cut off the concentrated product exiting the hollow cylinder 11 and direct it to the product chute 33.

Flush feeds suitable for the subject invention can be any gas or liquid capable of clearing the product chute of obstructions. In a preferred embodiment, the flush feed may comprise an inert gas, including, but not limited to, nitrogen or carbon dioxide. In another preferred embodiment, the flush feed comprises air or hydrogen. In yet another preferred embodiment, the flush feed may comprise at least a portion of the filtrate produced during the solid-liquid separation process either according to the subject invention or from a conventional solid-separation device, such as, for example, a centrifuge. In the case of separating para-xylene crystals from a slurry of mixed xylenes, the flush feed may comprise para-xylene.

During practice of the solid-liquid separation process, as described herein, the slurry feed is injected into the filter column at a pressure sufficient to separate solids from liquid and transport solids out of the filter column. The displacement fluid is injected into the filter column at an opposing pressure sufficient to facilitate the separation of solids from liquids and for at least a portion of the displacement fluid to pass through a filter to the interior of a filter tube. Within the filter column, the highest imparted pressure is generally at the slurry feed inlet, the lowest imparted pressure is generally at one or more filters of the filter column at the interior of one or more filter tubes, and the pressure at the product chute is at an intermediate level. Since fluids flow in the direction of high pressure to low pressure, this ensures that the fluid(s) in the filter column move towards the filters. When solid particles are suspended in liquid, they move in the same direction as the nearby liquid. As the fluid passes through the filter, the solid particles moving with the liquid begin to deposit, or otherwise form a dense phase or solid packed bed at, around or substantially near the filter within the hollow cylinder of the filter column. For the purposes of the present invention, a dense phase defines an area of solid particle concentration within the hollow cylinder (or higher pressure zone or higher concentration zone) having a greater concentration of solid particles than the slurry feed. The dense phase may define a solid packed bed wherein the solid particles are of such concentration that the solid particles move essentially as a solid body within the filter column.

When solid particles are deposited as a solid packed bed, the solid particles generally move in the same direction as the solid packed bed as opposed to the direction of fluid flow towards the filters. Notwithstanding, some particles may be carried out from the solid packed bed by the exiting liquid as it passes through the openings in the filters. Nevertheless, the solid packed bed moves essentially as a solid body, although its position in the filter column may remain substantially constant at steady state.

The direction that the bed moves, or whether the bed moves at all, is generally determined by the summation of all forces that act on the bed. One force that is imparted on the bed is from the liquid in the slurry feed that flows through the bed on the way to the filters. An opposing force is imparted on the bed from fluid(s) and displacement fluid flowing to the filters from the opposite end of the column. For purposes of the present invention, the displacement fluid provides hydraulic force if the displacement fluid is a liquid or pneumatic force if the displacement fluid is a gas. Therefore, the solid packed bed can be pushed by forces from both ends. The bed will move in the desired direction if the force imparted by the liquid in the slurry feed is larger than the sum of all the opposing forces. In addition, the opposing forces may also include the frictional forces imparted on the solid packed bed that act to impede movement of the solid packed bed and the force of gravity.

Referring again to FIG. 1, in a preferred embodiment, the slurry feed is injected into the closed end 13 of the hollow cylinder 11 of the filter column 10 via slurry feed inlet 27. The slurry feed flows through the hollow cylinder 11 towards the open end 15 of the hollow cylinder 11. A displacement fluid is directed into the chamber 25 via displacement fluid inlet 29. The displacement fluid flows countercurrently to the flow of the slurry feed in the hollow cylinder 11. As the slurry feed flows along one or more filters 23, the mother liquid in the slurry feed passes through at least one filter 23 into the interior of one or more filter tubes 17, producing a filtrate that exits the filter column 10 via the bottom portion 21 of at least one filter tube 17. Concurrently with the mother liquor, the displacement fluid passes through at least one filter 23 into the interior of one or more filter tubes 17 and exits the filter column 10 via the bottom portion 21 of at least one filter tube 17.

The filtrate exiting the filter column primarily comprises mother liquor, but may contain small amounts of solids from the slurry feed. The amount of solids present in the filtrate may be affected by such factors including, but not limited to, the type of filter employed in the filter column, the size of the openings in the filter, and the type of slurry feed injected into the filter column. However, it is preferred that the filtrate comprise no more than about 20 weight percent solids, more preferably no more than about 10 weight percent solids, even more preferably no more than about 5 weight percent solids, and most preferably no more than about 1 weight percent solids for best results. The balance of the filtrate is mother liquor. In the case of separating crystallized para-xylene from a slurry feed, the filtrate may comprise ortho-xylene, meta-xylene, ethylbenzene and/or para-xylene.

As the mother liquid passes through the filter 23, a dense phase within the hollow cylinder 11 generally forms. Preferably, the dense phase comprises a solid packed bed within the hollow cylinder 11 of the filter column 10 exterior to one or more filter tubes 17. Once the solid packed bed is formed, the solid packed bed moves towards the open end 15 of the hollow cylinder 11 where it is preferably removed from the filter column via one or more product chutes 33 as a concentrated product. In a preferred embodiment, the solid packed bed may be cut and pushed towards one or more product chutes 33 by one or more movable blades (not shown) as the solid packed bed exits the open end 15 of the hollow cylinder 11.

The concentrated product exiting one or more product chutes 33 primarily comprises solids from the slurry feed, but may comprise small amounts of mother liquor and displacement fluid. The amount of mother liquor (residual liquid) present in the concentrated product may be affected by such factors including, but not limited to, the type and size of the solids in the slurry feed, the size of the pores in the filter, the flow rate of the slurry feed injected into the filter column, and the type and flow rate of the displacement fluid. However, it is preferred that the concentrated solid product comprise less than about 40 weight percent mother liquor, preferably less than about 35 weight percent mother liquor, more preferably less than about 30 weight percent mother liquor, even more preferably less than about 25 weight percent mother liquor, even more preferably less than about 20 weight percent mother liquor, even more preferably less than about 15 weight percent mother liquor, even more preferably less than about 10 weight percent mother liquor, and most preferably less than about 5 weight percent mother liquor for best results.

In a preferred embodiment, the present invention is directed to maintaining a solid phase throughout the solid-liquid separation process by maintaining the higher pressure zone at a temperature lower than the melting point of at least one solid in the slurry. For the purposes of the present invention, the temperature of the higher pressure zone can be determined by determining the temperature of the concentrated product removed from the filter column or by placing temperature indicators in strategic locations within the higher pressure zone.

Referring now to FIGS. 2a-d, in a preferred embodiment, start-up of the solid-liquid separation process is preferably conducted in a manner to form an initial solid packed bed within the hollow cylinder 11 of the filter column 10. In this embodiment, as shown in FIG. 2a, the slurry feed initially enters the closed end 13 of the hollow cylinder 11 through one or more slurry feed inlets and a displacement fluid initially enters the open end 15 of the cylinder. The displacement fluid initially enters the hollow cylinder 11 at a pressure sufficient for at least a portion of the displacement fluid to pass through a filter to the lower pressure zone. The slurry feed moves towards the open end of the hollow cylinder 11 crossing at least one filter 23 wherein at least a portion of the mother liquor of the slurry passes through at least one filter 23, forming a filtrate that exits the filter column through a bottom portion 21 of the filter tube 17 that extends through the closed end of the filter column. The opposing pressure of the displacement fluid preferably prevents the slurry feed from completely crossing the filter 23 on its way towards the open end 15 of the hollow cylinder 11. Referring now to FIG. 2b, as the mother liquor of the slurry feed passes through the filter 23, the solids begin to form a dense phase 35 within the hollow cylinder 11. As the solids concentration of dense phase increases, as shown in FIG. 2c, a solid packed bed 37 preferably begins to form within the hollow cylinder 11. Once the solid packed bed 37 is formed, the pressure imparted by the slurry feed is generally greater than the pressure exerted by the displacement fluid. As a result, as shown in FIG. 2d, the solid packed bed 37 moves towards the open end 15 of the hollow cylinder 11.

The present invention provides for efficient separation of crystallized products from a slurry feed stream at relatively low temperatures without risk and attendant penalties associated with freezing a wash liquid within the filter column and causing complete failure of the solid-liquid separation process.

The present invention also provides for a substantial reduction in capital expenditure and routine maintenance by reducing the number of moving parts required by solid-liquid separation process units, such as screen bowl and pusher centrifuges. The filter column, according to the present invention, can comprise little or no moving parts, substantially reducing the routine maintenance costs associated with conventional solid-liquid separation units.

The present invention also provides for substantial savings in refrigeration costs by allowing for solid-liquid separation of crystallization products under substantially isothermal conditions. Current solid-liquid processes, such as screen bowl centrifuges, add considerable amounts of energy to the process stream thereby raising the temperature of the effluent streams. In a para-xylene crystallization process, for example, this energy added to the process requires increased refrigeration costs.

The present invention also provides for a substantial cost savings by reducing the amount of solids lost in filtrate streams frequently found in conventional solid-liquid separation processes and apparatuses.

The present invention also provides for the capability of varying the purity of a solid product separated from a slurry feed by simply varying the flow rate of the displacement fluid that is directed in countercurrent relation to the slurry feed.

Although the present invention has been described with particularity and detail, the following example provide further illustration of the invention and are understood not to limit the scope of the invention.

EXAMPLE

Example 1 illustrates a process for the purification of para-xylene substantially in accordance with the present invention and FIG. 1. The example encompassed an 8-hour run in which the following parameters were measured or calculated from the measured variables: (1) the weight percent of para-xylene in the slurry feed; (2) the solid-liquid content of the slurry feed; (3) the temperature of the slurry feed; (4) the weight percent of para-xylene in the filtrate; (5) the solid-liquid content of the filtrate; (6) the temperature of the filtrate; (7) the weight percent of para-xylene in the cake (concentrated product); (8) the solid-liquid content of the cake; and (9) the temperature of the cake.

The slurry feed comprised mixed xylenes from a commercial, low temperature crystallizer. The pressure of the slurry feed entering the filter column was 210 psia at the end of the run. The feed rate of the slurry feed was held constant throughout the run at 700 lb/hr. The temperature of the feed was about −81° F.

The displacement fluid was gaseous nitrogen. The feed rate of the nitrogen was 1.8 lb/hr. The temperature of the nitrogen varied throughout the run, but averaged about 0° F. The pressure of the nitrogen entering the filter column was 65 psia at end of run.

The filter column had a length of 25 inches and the hollow cylinder (higher pressure zone) had an inner diameter of 3.07 inches. The filter column contained a filter tube with an outsider diameter of 1.00 inches. The filter tube comprised a filter screen fabricated with a 316 stainless steel perforated sheet measuring 6 inches in length. The filter was located 7 inches, as measured from the top of the filter to the top of the filter tube. The filter comprised 9 mil. diameter openings in a staggered orientation with a center-to-center spacing of 0.015 inches. The overall open area of the filter was 31 percent. The pressure of the interior of the filter tubes throughout the run averaged 14.7 psia.

During the 8-hour run, five samples were removed, yielding the following results in the Table:

TABLE

| Sample | 1 | 2 | 3 | 4 | 5 |
| --- | --- | --- | --- | --- | --- |
| Hours fr m Start-up | 1.0 | 3.5 | 5.0 | 6.5 | 8.0 |
| Feed: wt. % pX content | 23.6 | 23.9 | 23.1 | 23.1 | 22.9 |
| Feed: Solid-liquid content | 16.0 wt. % solids; 84.0 wt. % liquids | 16.5 wt. % solids; 83.5 wt. % liquids | 15.6 wt. % solids; 84.4 wt. % liquids | 15.6 wt. % solids; 84.4 wt. % liquids | 15.4 wt. % solids; 84.6 wt. % liquids |
| Feed: Temperature | −80.4° F. | −81.1° F. | −81.5° F. | −81.4° F. | −81.3° F. |
| Filtrate: wt. % pX Content | 10.2 | 9.6 | 10.2 | 9.6 | 9.4 |
| Filtrate: Solid-liquid Content | 1.2 wt. % solids; 98.8 wt. % liquid | 0.7 wt. % solids; 99.3 wt. % liquid | 0.6 wt. % solids; 99.4 wt. % liquid | 0.5 wt. % solids; 99.5 wt. % liquid | 0.5 wt. % solids; 99.5 wt. % liquid |
| Filtrate: Temperature | −78.8° F. | −79.2° F. | −79.9° F. | −79.6° F. | −79.3° F. |
| Cake: wt. % pX Content | 82.2 | 83.1 | 84.1 | 83.3 | 83.9 |
| Cake: Solid-liquid Content | 80.4 wt. % solids; 19.6 wt. % liquid | 81.4 wt. % solids; 18.6 wt. % liquid | 82.6 wt. % solids; 17.4 wt. % liquid | 81.7 wt. % solids; 18.3 wt. % liquid | 83.9 wt. % solids; 17.7 wt. % liquid |
| Cake: Temperature | −78.3° F. | −78.2° F. | −78.4° F. | −78.3° F. | −78.3° F. |

SUMMARY OF THE EXAMPLE

The Table shows that very little solids were present in the filtrate during the separation process. The amount of para-xylene present in the filtrate was primarily derived from liquid para-xylene present in the slurry feed with a small portion deriving from solids escaping through the filter. Additionally, the para-xylene cake had sufficient solid content at a temperature substantially near the temperature of the slurry feed to be further processed, providing for substantial savings in refrigeration costs.

It is believed that a para-xylene wash liquid would not be a suitable displacement fluid for the purification of para-xylene under the process conditions utilized in the Example. More particularly, it is believed that the use of a para-xylene wash liquid would freeze within the filter column clogging the openings of the filter. This is primarily due to the low operating temperature of the purification process of the Example, which is far below the melting point of para-xylene. It is believed that the clogged filter would result in a rapid increase within the hollow cylinder of the filter, prompting shut down of the process prior to the point of filter column damage from excessive pressure.

Although embodiments of this invention have been shown and described, it is to be understood that various modifications and substitutions, as well as rearrangement of parts and equipment, can be made by those skilled in the art without departing from the novel spirit and the scope of this invention.

That which is claimed is:

1. A process for separating solids from liquids in a filtration zone defining a higher concentration zone and a lower concentration zone, the zones being separated from one another by a filter, the process comprising the simultaneous steps of:
    (a) flowing a slurry feed comprising a liquid and a solid into the higher concentration zone;
    (b) flowing a displacement fluid to the higher concentration zone countercurrent to the flow of the slurry feed; and
    (c) removing at least a portion of the liquid through the filter to the lower concentration zone;
wherein the displacement fluid is insoluble in the slurry feed components and displaces at least a portion of the liquid from the slurry feed past the filter and into the lower concentration zone to produce a filtrate in the lower concentration zone.

2. The process of claim 1, wherein the displacement fluid is a gas.

3. The process of claim 2, further comprising the step of flowing at least a portion of the gas from the higher concentration zone through the filter and into the lower concentration zone.

4. The process of claim 2, wherein the slurry feed comprises a product from a crystallization process.

5. The process of claim 4, wherein the slurry feed comprises para-xylene.

6. The process of claim 2, wherein the filtrate comprises at least one of ortho-xylene, meta-xylene and para-xylene.

7. The process of claim 2, wherein the gas displaces at least a portion of the liquid from the slurry to form a dense phase in the higher concentration zone.

8. The process of claim 7, wherein the dense phase comprises a solid packed bed.

9. The process of claim 1, further comprising the step of flowing at least a portion of the displacement fluid from the higher concentration zone through the filter and into the lower concentration zone.

10. The process of claim 1, wherein the slurry feed comprises a product from a crystallization process.

11. The process of claim 10, wherein the slurry feed comprises para-xylene.

12. The process of claim 1, wherein the filtrate comprises at least one of ortho-xylene, meta-xylene and para-xylene.

13. The process of claim 1, wherein the displacement fluid displaces at least a portion of the liquid from the slurry to form a dense phase in the higher concentration zone.

14. The process of claim 13, wherein the dense phase comprises a solid packed bed.

15. A solid-liquid separation process comprising simultaneously:
    (a) flowing a slurry feed into a hollow cylinder of a filter column comprising the hollow cylinder and at least one filter tube disposed in the hollow cylinder and extending in an axial direction within the hollow cylinder, wherein the at least one filter tube comprises an integrally attached filter, the filter forming a direct connection between an interior of the tube and an interior of the hollow cylinder; and,
    (b) directing a displacement fluid insoluble in components of the slurry feed into the hollow cylinder countercurrent to the flow of the slurry feed,
wherein substantial portions of the displacement fluid and liquid in the slurry feed flow through the filter to form a filtrate inside of the at least one filter tube and a dense phase outside of the at least one filter tube.

16. The process of claim 15, wherein the displacement fluid is a gas.

17. The process of claim 16, wherein the slurry feed comprises para-xylene.

18. The process of claim 15, wherein the slurry feed comprises para-xylene.

19. The process of claim 15, wherein the dense phase comprises a solid packed bed.

20. The process of claim 19, wherein at least a portion of the gas passes through at least a portion of the solid packed bed to the filter.

* * * * *